United States Patent [19]
Lennon

[11] Patent Number: 5,859,290
[45] Date of Patent: Jan. 12, 1999

[54] HYDROGENATION OF CYANOPHOSPHONATE DERIVATIVES IN THE PRESENCE OF A GLYCINE DERIVATIVE

[75] Inventor: Patrick J. Lennon, Webster Grove, Mo.

[73] Assignee: Monsanto Company, St. Louis, Mo.

[21] Appl. No.: 997,340

[22] Filed: Dec. 23, 1997

Related U.S. Application Data

[60] Provisional application No. 60/034,522 Dec. 30, 1996.
[51] Int. Cl.$^6$ .................................................. C07F 562/17
[52] U.S. Cl. .................................................. 562/17
[58] Field of Search .............................................. 562/17

[56] References Cited

U.S. PATENT DOCUMENTS

| | | | |
|---|---|---|---|
| 2,402,703 | 6/1946 | Woodstock . | |
| 2,702,299 | 2/1955 | Harris . | |
| 3,432,277 | 3/1969 | Roesky | 23/357 |
| 3,812,221 | 5/1974 | Braden et al. | 260/968 |
| 4,221,583 | 9/1980 | Gaertner et al. . | |
| 4,568,432 | 2/1986 | Rogers . | |
| 5,679,843 | 10/1997 | Hodgkinson et al. | 562/17 |

FOREIGN PATENT DOCUMENTS

| | | | |
|---|---|---|---|
| 300 936 | 9/1992 | Germany | C07F 9/40 |
| 96/15135 | 5/1996 | WIPO . | |

OTHER PUBLICATIONS

Abstract—Database WPI, Section Ch, Week 7615, Derwent Publications Ltd., London, GB; Class B04, AN 76–27192X, XP002061354 & JP 51 023 255 A (Nippon Chem. Ind. Co. Ltd.), 24 Feb. 1976.

Blanchard, J. "Préparation d–acides beta–amino–ethyl–phosphoniques" *Tetrahedon;* vol. 32, NO. 4, 1976, Oxford GB, pp. 455–459, XP002061374.

Chemical Abstracts, vol. 093, No. 12, 22 Sep. 1980, Columbus, Ohio, US; abstract No. 123612, Zhurba, Y.I. et al. "Increase in the stability of silver complexes in the process of simultaneous developing and fixing" and ZH Nauchn, Pirkl. Fotogr. Kinematogr. (ZNPFAG, 00444561); 80; vol. 25(3); pp. 182–185, Vses. Gos. Nauchno–Issled. Proektn. Inst. Khim.–Fotogr. Prom., Moscow; USSR; XP0020612352.

Dyatkina, N. et al., Synthesis and antiviral activity of some fluorinated nucleotide derivativers: Nucleosides Nucleotides (NUNUD5, 07328311); 94; col. 13 (1–3); pp. 325–337, Engelhardt Inst. Mol. Biol.; Mowcow; 117984, Russia XP002061348, 1994.

Kashemirov, B.A. "(E)–(Hydroxyimino)(hydroxymethoxyphosphinyl)acetic acid: Synthesis and pH dependent fragmentation," *Tetrahedron Letters,* vol. 36, No. 52, Oxford GB, pp. 9437–9440, XP002061351.

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem.* 552:132–156 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc.* 117:7285–7286 (1995).

Shiori et al., "Reaction of Diethyl Phosphorocyanidate(DEPC) with Carboxylic Acids. A New Synthesis of Carboxylic Esters and Amides," *Tetrahedron* 3(18):2211–2217 (1976).

Tung et al., "A New Method for the Preparation of O,O'–Dialkylphosphoryl Cyanides," *Hua Hsueh Hsueh Pao (Acta Chimica Sinica)* 31(3): 199–202 (1965).

*Primary Examiner*—Samuel Barts
*Attorney, Agent, or Firm*—James M. Warner; Arnold, White & Durkee

[57] ABSTRACT

A process for preparing N-phosphonomethylglycine or an N-phosphonomethylglycine derivative involves the hydrogenation of cyanophosphonate derivatives in the presence of a glycine derivative and a catalyst to produce N-phosphonomethylglycine.

16 Claims, No Drawings

HYDROGENATION OF CYANOPHOSPHONATE DERIVATIVES IN THE PRESENCE OF A GLYCINE DERIVATIVE

This application claims the benefit of provisional application Ser. No. 60/034,522, filed Dec. 30, 1996.

BACKGROUND OF THE INVENTION

N-phosphonomethylglycine (glyphosate) is a highly effective commercial herbicide (available under the trade name Roundup™) useful for the control of a large variety of weeds.

There exists a need for improved synthetic routes towards the preparation of N-phosphonomethylglycine and its derivatives that offer fewer steps, higher yields, reduced waste materials or that avoid the use of halogenated precursors.

SUMMARY OF THE INVENTION

The invention relates to a novel method for preparing N-phosphonomethylglycine and its derivatives. More particularly, the invention is directed to a method for preparing N-phosphonomethylglycine and its derivatives that comprises contacting a cyanophosphonate derivative, hydrogen and a glycine derivative in the presence of a suitable catalyst.

The method according to the invention offers significant advantages in that it provides a novel, economic route to synthesize N-phosphonomethylglycine and its derivatives having an improved environmental impact over conventional processes using halogen-containing phosphorus compounds.

DESCRIPTION OF ILLUSTRATIVE EMBODIMENTS

The invention is directed to a method for preparing N-phosphonomethylglycine and its derivatives. More particularly, the invention is directed to a method for preparing N-phosphonomethylglycine and N-phosphonomethylglycine derivatives that comprises contacting a cyanophosphonate derivative, a glycine derivative and hydrogen in the presence of a catalyst.

In a preferred embodiment, the inventive process involves charging a reaction vessel with a cyanophosphonate derivative, a glycine derivative, hydrogen and a suitable catalyst under conditions sufficient to produce N-phosphonomethylglycine and/or at least one N-phosphonomethylglycine derivative. The hydrogenation can be performed at a temperature preferably in the range of about 10° C. to about 70° C., and more preferably in the range of about 20° C. to about 60° C. The hydrogenation step be performed for any period of time suitable for the preparation of N-phosphonomethylglycine. Preferably the hydrogenation will be performed for less than 24 hours, or more preferably, for less than about 12 hours.

The cyanophosphonate derivative is generally any cyanophosphonate derivative suitable for participating in the inventive process to produce N-phosphonomethylglycine or an N-phosphonomethylglycine derivative. In a preferred embodiment, the cyanophosphonate derivative is a cyanophosphonate disalt, a cyanophosphonate diester, a cyanophosphonate monosalt monoester, a cyanophosphonate monosalt monoacid, a cyanophosphonate monoester monoacid or cyanophosphonic acid. The cyanophosphonate derivative can be any of those disclosed or incorporated in co-pending U.S. application Ser. No. 08/997,339, entitled "Novel Cyanophosphonate Derivatives and Method for Their Preparation," by Patrick J. Lennon and Sergey G. Vulfson, filed Dec. 23, 1997, which is incorporated herein by reference.

Preferably, the cyanophosphonate disalt is disodium cyanophosphonate, dipotassium cyanophosphonate, dilithium cyanophosphonate, bis(2-hydroxyethylammonium) cyanophosphonate, bis(ammonium)cyanophosphonate, bis(isopropylammonium)cyanophosphonate, bis(dimethylammonium)cyanophosphonate, bis(trimethylsulfonium)cyanophosphonate or bis(dicyclohexylammonium)cyanophosphonate. The cyanophosphonate diester is preferably dimethyl cyanophosphonate, diethyl cyanophosphonate, diisopropyl cyanophosphonate or dicyclohexyl cyanophosphonate. The cyanophosphonate monosalt monoester is preferably sodium ethyl cyanophosphonate, potassium ethyl cyanophosphonate, sodium methyl cyanophosphonate, potassium methyl cyanophosphonate, sodium isopropyl cyanophosphonate, potassium isopropyl cyanophosphonate, sodium cyclohexyl cyanophosphonate or potassium cyclohexyl cyanophosphonate. The cyanophosphonate monosalt monoacid is preferably sodium hydrogen cyanophosphonate or potassium hydrogen cyanophosphonate. The cyanophosphonate monoester monoacid is preferably methyl hydrogen cyanophosphonate, ethyl hydrogen cyanophosphonate, isopropyl hydrogen cyanophosphonate or cyclohexyl hydrogen cyanophosphonate.

The solvent is generally any compound suitable for enhancing the solubility of the reactants or providing a medium for the reaction. In a preferred embodiment, the solvent is water.

The glycine derivative is preferably glycine, glycinamide, a glycine salt or a glycine ester. The glycine ester is preferably an alkyl ester or an arylalkyl ester. The glycine alkyl ester is preferably glycine methyl ester, glycine ethyl ester, glycine cyclohexyl ester or glycine t-butyl ester. The glycine arylalkyl ester is preferably glycine benzyl ester. The glycine salt is preferably glycine hydrochloride, glycine sodium salt or glycine potassium salt.

Hydrogen pressure can be maintained in the reaction system at a level suitable for the formation of N-phosphonomethylglycine, and consistent with the safety limitations of the process system. In a preferred embodiment, the hydrogen pressure is between about 1 and about 250 psi, more preferably between about 1 and about 100 psi, still more preferably between about 5 and about 50 psi and most preferably at about 25 psi.

The catalyst is generally any material effective at catalyzing the formation of N-phosphonomethylglycine in the inventive method. In a preferred embodiment, the catalyst is a transition metal catalyst. More preferably, the catalyst is palladium on carbon or palladium hydroxide on carbon. The catalyst can be used at a stoichiometric amount or catalytic amount with respect to the cyanophosphonate derivative. The stoichiometric amount is preferably between about 1 molar equivalent and 5 molar equivalents with respect to the cyanophosphonate derivative, and more preferably between about 1 molar equivalent and 2 molar equivalents with respect to the cyanophosphonate derivative. The catalytic amount is preferably between about 0.5 molar percent and 100 molar percent with respect to the cyanophosphonate derivative, and more preferably between about 0.5 molar percent and 50 molar percent with respect to the cyanophosphonate derivative.

The hydrogenation reaction mixture preferably further contains an acid in an amount sufficient to promote formation of the desired product. The acid can be an inorganic acid or an organic acid. The inorganic acid is preferably hydrochloric acid, sulfuric acid, phosphoric acid or nitric acid, and more preferably, hydrochloric acid. The organic acid is preferably acetic acid, trifluoroacetic acid, trifluoromethanesulfonic acid or p-toluenesulfonic acid. The acid can be present at a concentration between about 0.1 and 5 molar equivalents with respect to the cyanophosphonate derivative, more preferably at a concentration between about 0.5 and 2.5 molar equivalents with respect to the cyanophosphonate derivative, and most preferably at a concentration of about 1 molar equivalent or about 2 molar equivalents with respect to the cyanophosphonate derivative, depending on the degree of protonation.

The reaction mixture can further contain a magnesium salt. The magnesium salt is preferably magnesium bromide, magnesium chloride, magnesium iodide, magnesium trifluoromethane sulfonate, magnesium p-toluenesulfonate, magnesium acetate, magnesium tetrafluoroborate, magnesium hexafluorophosphate or magnesium trifluoroacetate. The magnesium salt can be present in a catalytic or stoichiometric amount with respect to the cyanophosphonate derivative. The catalytic amount is preferably between about 2 molar percent and about 100 molar percent with respect to the cyanophosphonate derivative, and more preferably between about 2 molar percent and about 50 molar percent with respect to the cyanophosphonate derivative. The stoichiometric amount is preferably between about 1 molar equivalents and 5 molar equivalents with respect to the cyanophosphonate derivative.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Hydrogenation of Disodium Cyanophosphonate and Glycine to N-phosphonomethylglycine Disodium cyanophosphonate (partially hydrated) (0.170 g, 1.06 mmol) was dissolved in water (5 ml) in a Fisher Porter bottle containing a magnetic stir bar, and glycine (0.0862 g, 1.148 mmol) was added. Three percent palladium on carbon (0.060 g, prepared as per Example 3) was added along with HCl-dioxane (0.25 ml, 4N, 1 mmol). After three pressure-release cycles with hydrogen, the bottle was pressurized to 25 psi with hydrogen and stirred overnight at ambient temperature. The pressure was released, and the reaction mixture was filtered through Celite and washed with $D_2O$. HPLC analysis (system for phosphate analysis) gave a 1.2% yield of N-phosphonomethylglycine.

Example 2

Hydrogenation of Dipotassium Cyanophosphonate and Glycine to N-phosphonomethylglycine Dipotassium cyanophosphonate (partially hydrated, 0.188 g, 1.03 mmol) was dissolved in water (5 ml) in a Fisher Porter bottle containing a magnetic stir bar, and glycine (0.0828 g, 1.10 mmol) was added. Palladium hydroxide 20% on carbon (0.089 g, Aldrich) was added along with HCl-dioxane, (0.25 ml, 4N, 1 mmol), and magnesium bromide (0.185 g, 1.00 mmol). After three pressure-release cycles with hydrogen, the bottle was pressurized to 25 psi with hydrogen and stirred overnight at 50° C. The pressure was then released, and the reaction mixture was filtered through Celite and washed with $D_2O$. HPLC analysis (system for phosphate analysis) gave a 2.2% yield of N-phosphonomethylglycine.

Example 3

Hydrogenation of Disodium Cynanophosphonate and Glycine Ethyl Ester to Ethyl N-phosphonomethylglycine Sodium lithium cyanophosphonate was dissolved in water in a Fisher Porter bottle containing a magnetic stir bar, and glycine ethyl ester was added. A catalyst of 5% palladium on carbon (Lot #323810, water 52.38%, Engelhard) was added. After three pressure-release cycles with hydrogen, the bottle was pressurized to 25 psi with hydrogen and stirred overnight at 50° C. The pressure was then released and the reaction mixture was filtered through Celite and washed with $D_2O$. HPLC analysis (system for phosphate analysis) gave a 0.93% yield of N-phosphonomethylglycine.

Example 4

Preparation of a Palladium on Carbon Catalyst

In a 1500 ml teflon round bottom flask, activated carbon (44.45 g, 1500 $m^2$/g surface area, 1.2 ml/g volume) was slurried with deionized water (360 ml) and a sodium hydroxide solution (3.72 g of a 50% w/v solution). In a 250 ml beaker, Pd(II) acetate (2.855 g) was dissolved in an aqueous ammonium hydroxide solution (125 ml, 28% $NH_3$ in water). The Pd(II) acetate solution was added to the slurry of activated carbon in the teflon flask over a period of 30 minutes, and the mixture was stirred for an additional 30 minutes while heating to 85°–90° C. An aqueous solution of formaldehyde (4.85 ml of 37% formaldehyde and 40 ml of deionized water) was added to the slurry over a 30 minute period, and the reaction mixture was held at 85°–90° C. for an additional 90 minutes. After cooling to ambient temperature, the reaction mixture was filtered to remove the Pd on carbon catalyst. The catalyst was washed with deionized water (300 ml) and dried in a vacuum oven overnight at 125° C.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the process described herein without departing from the concept, spirit and scope of the invention. All such similar substitutes and modifications apparent to those skilled in the art are deemed to be within the spirit, scope and concept of the invention.

What is claimed is:

1. A method for preparing N-phosphonomethylglycine or an N-phosphonomethylglycine derivative comprising:
   contacting a cyanophosphonate derivative, a glycine derivative, hydrogen and a suitable catalyst in a reaction mixture under sufficient conditions to produce N-phosphonomethylglycine or an N-phosphonomethylglycine derivative.

2. The method of claim 1, wherein the cyanophosphonate derivative is a cyanophosphonate disalt, a cyanophosphonate diester, a cyanophosphonate monoester monosalt, a cyanophosphonate monosalt monoacid, a cyanophosphonate monoester monoacid or cyanophosphonic acid.

3. The method of claim 2, wherein the cyanophosphonate derivative is disodium cyanophosphonate.

4. The method of claim 1, wherein the glycine derivative is glycine.

5. The method of claim 1, wherein the glycine derivative is a glycine ester.

6. The method of claim 5, wherein the glycine ester is a glycine ethyl ester and the N-phosphonomethylglycine derivative is ethyl N-phosphonomethylglycine.

7. The method of claim 1, wherein the reaction mixture further comprises a solvent.

8. The method of claim 7, wherein the solvent is water.

9. The method of claim 1, wherein the catalyst is a palladium on carbon catalyst.

10. The method of claim 1, wherein the catalyst is a palladium hydroxide on carbon catalyst.

11. The method of claim 1, wherein the reaction mixture further contains an acid.

12. The method of claim 11, wherein the acid is hydrochloric acid.

13. The method of claim 1, wherein the reaction mixture further contains a magnesium salt.

14. The method of claim 13, wherein the magnesium salt is magnesium bromide.

15. The method of claim 1, wherein the hydrogen is added to the reaction mixture at a pressure between about 1 and about 100 psi.

16. The method of claim 1, wherein the temperature of the reaction mixture is between about 10° C. and about 70° C.

* * * * *